(12) United States Patent
Weisshaupt et al.

(10) Patent No.: US 10,092,347 B2
(45) Date of Patent: Oct. 9, 2018

(54) MEDICAL TFT INSTRUMENT COMPRISING A PIVOTABLE ELECTRODE SUPPORT

(71) Applicant: Aesculap AG, Tuttlingen (DE)

(72) Inventors: Dieter Weisshaupt, Immendingen (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 491 days.

(21) Appl. No.: 14/388,925

(22) PCT Filed: Apr. 12, 2013

(86) PCT No.: PCT/EP2013/057662
§ 371 (c)(1),
(2) Date: Sep. 29, 2014

(87) PCT Pub. No.: WO2013/156400
PCT Pub. Date: Oct. 24, 2013

(65) Prior Publication Data
US 2015/0088131 A1    Mar. 26, 2015

(30) Foreign Application Priority Data
Apr. 20, 2012   (DE) .................. 10 2012 103 503

(51) Int. Cl.
*A61B 18/14*     (2006.01)
*A61B 18/00*     (2006.01)
*A61B 18/12*     (2006.01)

(52) U.S. Cl.
CPC .. *A61B 18/1442* (2013.01); *A61B 2018/0063* (2013.01); *A61B 2018/00607* (2013.01);
(Continued)

(58) Field of Classification Search
CPC ............ A61B 18/085; A61B 2018/145; A61B 18/1445; A61B 18/1442; A61B 2018/1495
See application file for complete search history.

(56) References Cited

U.S. PATENT DOCUMENTS

| 6,102,909 | A  | * | 8/2000 | Chen  | A61B 17/2804 606/170 |
| 6,858,028 | B2 | * | 2/2005 | Mulier | A61B 18/1445 128/898 |

(Continued)

FOREIGN PATENT DOCUMENTS

| CN | 102083386 | 6/2011 |
| CN | 102368956 | 3/2012 |

(Continued)

OTHER PUBLICATIONS

Chinese Office Action dated Jun. 16, 2015 in Chinese Application No. 201380020935.X, including English translation.
(Continued)

*Primary Examiner* — Daniel Fowler
*Assistant Examiner* — Ryan T Clark
(74) *Attorney, Agent, or Firm* — RatnerPrestia

(57) ABSTRACT

A manually operable HF instrument in bipolar construction includes a jaw part having two electrode legs which can be moved relative to each other like pincers or scissors, and an instrument handle for operating and activating the jaw part. A separate electrode mount is articulated on at least one electrode leg of the jaw part so as to be able to pivot relative to it, an electrode in turn being elastically/pliably installed on the electrode mount.

13 Claims, 3 Drawing Sheets

Figure 1:
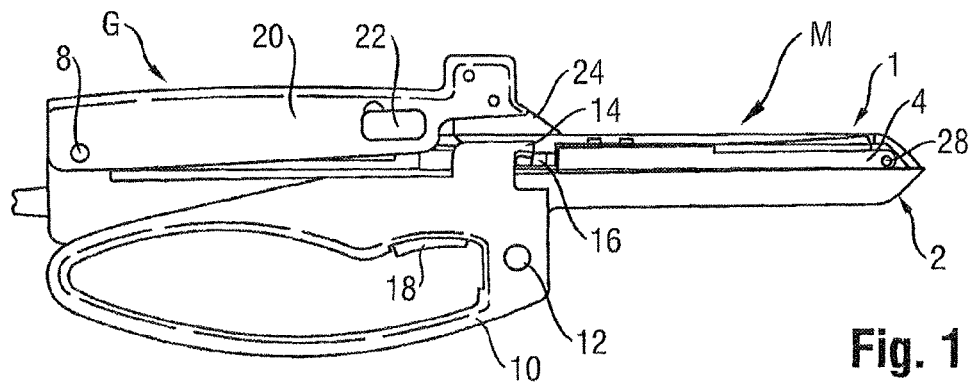

(52) U.S. Cl.
CPC ............... *A61B 2018/00619* (2013.01); *A61B 2018/126* (2013.01); *A61B 2018/145* (2013.01); *A61B 2018/1455* (2013.01)

(56) References Cited

U.S. PATENT DOCUMENTS

| | | | |
|---|---|---|---|
| 8,696,662 B2 | 4/2014 | Eder | |
| 2005/0090817 A1* | 4/2005 | Phan | A61B 18/1445 606/41 |
| 2006/0217697 A1 | 9/2006 | Lau et al. | |
| 2006/0259054 A1 | 11/2006 | Masuda et al. | |
| 2007/0043297 A1 | 2/2007 | Miyazawa | |
| 2007/0213711 A1* | 9/2007 | Eder | A61B 18/1442 606/51 |
| 2008/0183251 A1 | 7/2008 | Azar et al. | |
| 2009/0131934 A1* | 5/2009 | Odom | A61B 18/1445 606/51 |
| 2009/0204114 A1 | 8/2009 | Odom | |
| 2010/0057081 A1* | 3/2010 | Hanna | A61B 18/1445 606/51 |
| 2010/0057082 A1* | 3/2010 | Hanna | A61B 18/1445 606/51 |
| 2010/0057083 A1* | 3/2010 | Hanna | A61B 18/1445 606/51 |
| 2010/0057084 A1* | 3/2010 | Hanna | A61B 18/1445 606/51 |
| 2010/0185197 A1* | 7/2010 | Sakao | A61B 18/085 606/51 |
| 2011/0184404 A1* | 7/2011 | Walberg | A61B 18/1445 606/33 |
| 2011/0251609 A1* | 10/2011 | Johnson | A61B 17/2804 606/46 |
| 2011/0278343 A1 | 11/2011 | Knodel | |
| 2014/0214025 A1* | 7/2014 | Worrell | A61B 18/1445 606/41 |

FOREIGN PATENT DOCUMENTS

| | | |
|---|---|---|
| DE | 102008008309 A1 | 8/2009 |
| DE | 102010031569 A1 | 2/2011 |
| EP | 2158867 A1 | 3/2010 |
| JP | 2011200586 | 10/2011 |
| WO | WO 2007/103986 | 9/2007 |
| WO | 2010084684 | 7/2010 |
| WO | WO 2010/088044 | 8/2010 |
| WO | 2011097469 | 8/2011 |

OTHER PUBLICATIONS

Japanese Office Action dated Sep. 8, 2015 for Japanese Application No. 2015-506190, including English translation.

German Search Report with partial translation issued in related German Application No. 10 2012 103 503.2, dated Oct. 30, 2012.

International Search Report with partial translation issued in related International Application No. PCT/EP2013/057662, dated Jun. 18, 2013.

International Preliminary Report on Patentability issued in related International Application No. PCT/EP2013/057662, dated Oct. 21, 2014.

English Translation of Communication under Rule 71(3) EPC in related European Application No. 13 716 281.4, dated Aug. 8, 2014.

* cited by examiner

MEDICAL TFT INSTRUMENT COMPRISING A PIVOTABLE ELECTRODE SUPPORT

RELATED APPLICATIONS

This application is the U.S. National Phase of International Application No. PCT/EP2013/057662, filed Apr. 12, 2013, which claims the benefit of priority of German Application No. DE 10 2012 103 503.2, filed Apr. 20, 2012, the contents of both applications being incorporated by reference herein in their entireties.

FIELD

The present invention relates generally to a medical HF instrument (TFT instrument), and more specifically to a medical HF instrument in bipolar construction.

BACKGROUND

In high-frequency surgery, in the following also referred to as HF surgery, an alternating current having a high frequency is guided through the human body or a certain tissue area of the human body in order to specifically damage or cut the tissue at a defined place. A substantial advantage over a conventional cutting technology using a scalpel is that the bleeding can be arrested by closing the affected vessels during the cutting process. During resecting tissue, for example, such as in the event of a partial lung resection or hepatic lobe resection, such an intervention is therefore not carried out as usual by means of a clip suture device; rather, the tissue is "welded" or "sealed" by means of the HF current of such a TFT instrument. The advantage of this method is to be seen clearly in the fact that there are no implants (e.g. metal clips) which remain in the body.

Basically, HF electro-surgery can be divided into two application techniques, which are the monopolar application technique and the bipolar application technique.

The monopolar technology is still the most common technique in use. Here, one pole of the HF voltage source is connected to the patient via a surface area which is as large as possible. This electrode is referred to as the neutral electrode. The other pole is the actual surgical instrument (active electrode) which is manually guided by the surgeon. The current flows through the path with the smallest resistance from the active electrode to the neutral electrode. In the direct vicinity of the active electrode, the current density is highest, which is the place where the strongest thermal effect occurs.

The neutral electrode is shaped with a surface area as large as possible, so that the current density in the body is kept small and no burns will occur. Due to the large surface area, the skin on the neutral electrode is not noticeably heated.

With the bipolar technology and in contrast to the monopolar technology, the current flows only through a small part of the body—in fact through that part where the surgical impact (cut or coagulation) is desired. Two electrodes which are isolated with respect to each other and between which the HF voltage is applied, are directly brought to the site of operation. The electrical circuit is closed via the tissue situated in between. The thermal effect will then occur in the tissue between the electrodes.

As compared to the monopolar technology, 20-30% less power is required. The surrounding tissue will not be damaged as there is no current flow, and any measuring equipment on the patient (e.g. ECG) will not be disturbed. Therefore, this procedure is particularly well suited for critical and precise applications such as in micro, neuro and ENT surgery.

In order to avoid a failure of the sealed or welded portion of the tissue, especially in the bipolar application technique, the parameters acting on the tissue have to be detected and adjusted on the instrument as precisely as possible. In order to ensure this, an exact monitoring of the following parameters is indispensable:

temperature on/in the tissue between the electrodes,
clamping pressure exerted on the tissue by the electrodes,
tissue impedance,
mutual electrode distance, and possibly
position of the instrument or position of the electrodes relative to each other.

For those frequencies which are used in HF surgery, the body tissue behaves like an ohmic resistance. Here, the specific resistance highly depends on the type of the tissue, with the power input for the same temperature increase of the tissue being directly proportional to the specific resistance. The specific resistance of muscle tissue and highly perfused tissue is relatively low. The specific resistance of fat is higher by about factor 15 and the one of bones by factor 1000. The effective resistance, however, also depends on the type and the shape of the electrodes as well as on the intended degree of destruction of the tissue. Thus, the form and the level of the current have to be exactly adapted to the type of the tissue where the operation is carried out as well as to the employed electrodes and should yield a constant and uniform result throughout the entire electrode length.

The quick and efficient arrest of bleeding with coagulation application is used if there is no spontaneous coagulation and replaces—for small vessels—in most cases the costly fibrin sealants or the expensive ligature. The term "coagulation" includes two different surgical techniques here: The in-depth coagulation and the (electrical) arrest of bleeding.

In the in-depth coagulation, the tissue is heated up in large areas to 50-80° C. This is carried out with ball, plate or roller type electrodes and serves for the subsequent ablation of the tissue. In this process, a high current density and a current without impulse modulation are used. The coagulation depth can be influenced by the magnitude of the amperage.

For stopping bleeding, an impulse-modulated HF current is used on clamps and forceps. The blood vessels are gripped with the tips of the tools and constricted through dehydration until they are completely closed. This is carried out in the bipolar mode, in rare cases monopolar forceps are used.

The process of cutting the tissue (instead of cutting with the scalpel) is referred to as electrotomy in HF surgery. During the cutting process, the HF surgical device (TFT instrument) is operated in the monopolar mode with a needle or narrow lamella (blade). Recently, also bipolar scissors are applied with great success for cutting.

Related state of the art is known from the documents DE 10 2008 008 309 A1, DE 10 2010 031 569 A1 and US 2008/0 183 251 A1. The reference DE 10 2010 031 569 A1 discloses an electrosurgical instrument for cutting and sealing tissue, the instrument comprising:

a) a first and a second cheek element in opposing relationship relative to each other, the first cheek element comprising an inner surface adapted to cooperate with the inner surface of the second cheek element in order to grip tissue therebetween; at least one of the cheek elements is movable with respect to the other one, so that the cheek elements are selectively operable between an open position in which the cheek elements are arranged in a spaced relationship relative to each other, and a closed position in which the inner surfaces of the cheek elements work together to grip the tissue between them;

b) means for causing a movement of the one or each cheek element, in order to operate the cheek elements between the open and closed positions;

c) a first electrode as the coagulation electrode on the inner surface of the one of the cheek elements;

d) a second electrode as the coagulation electrode on the inner surface of the one of the cheek elements;

e) an isolation element separating the first and second electrodes, the first and second electrodes being connectable to opposite poles of an electrosurgical generator;

f) a third electrode as the cutting electrode on the inner surface of the first cheek element, the third electrode being connectable to a pole of the electrosurgical generator; and g) a fourth electrode on an external surface of the first cheek element separate from the inner surface, the fourth electrode being connectable to a pole of the electro-surgical generator;

the electrosurgical instrument being capable of selectively causing a coagulation of the tissue between the first and second electrodes and/or a process of cutting the tissue touched by the third electrode and/or a treatment of the tissue touched by the fourth electrode.

With the surgical HF instruments (TFT instruments) of the bipolar type, however, preferably consisting of two electrode legs which can pivot in the manner of scissors or pincers, there is the basic problem that the opposing HF electrodes (sealing/welding electrodes) are not in an exactly parallel orientation upon closing the jaw part comprised of the electrode legs, so that the clamping pressure exerted on the tissue clamped therebetween is not homogenous along the electrodes. As the clamping pressure is one of those above-mentioned parameters having an evidently large influence on the treatment outcome, an inhomogenous clamping pressure has a negative impact on the seam quality along the two electrodes. In addition, an irregular gap width implies an irregular flow of current over the electrode length, which is also disadvantageous for the treatment outcome (coagulation quality). Here, the influences of the mentioned parameters on the treatment outcome are so strong that already small deviations from the optimum values can have significant effects.

SUMMARY

In view of this set of problems, it is the object of the present invention to provide a surgical bipolar HF instrument (TFT instrument), preferably in the type of scissors or pincers, in which the opposing and cooperating HF electrodes are parallel to each other upon closing the jaw part, which is supposed to establish constant prerequisites for HF surgery (tissue impedance) throughout the effective electrode length. Here, one aim is to be able to electrically control the quality of the sealed/welded tissue portions in a more exact way.

This object is achieved by a medical HF instrument in accordance with the invention.

According to one aspect of the present invention, a medical HF instrument in bipolar construction is suggested for achieving the afore-mentioned object, said instrument comprising two electrode legs or electrode (base) carriers which can be moved toward each other and are each provided with at least one longitudinally extending electrode or electrode array (coagulation electrodes or coagulation electrode arrays) facing each other. At least one electrode or electrode array is installed on a separate electrode mount which is supported (possibly in floating manner) on one of the electrode legs/electrode base carriers in a rotatable, pivotable or tilting fashion, thus being able to align preferably in self-acting manner to be parallel to the opposing electrode, or which is adjusted—in coordination with the movement of the electrode legs/base carriers as well as with the intended gap width between the electrodes in the closed state of the instrument—in such a manner that a parallel orientation of the electrodes is achieved in the closed state of the instrument. According to the invention, at least said one electrode or electrode array (throughout its electrode length) mounted on the separate electrode mount is elastically/pliantly installed on the separate electrode mount. Due to said installed spring mechanism between the at least one electrode and the separate electrode mount, the parallelism of the electrodes in the closed state of the instrument is further improved, so that the distance of the electrodes is made equal along the entire effective length. Owing to the electrode spacing which is adjusted/can be adjusted to be substantially constant over the electrode length, it automatically results in the (clamped) tissue being uniformly penetrated by HF energy.

The advantages which can be reached here may be summarized as follows:

First, any not intended (excessive or too low) tissue damages which could be produced by an excessive/reduced force impact on the clamped tissue are avoided. This means that the clamping pressure exerted by the electrodes can be principally controlled in a better way.

A reliable fusion of the individual tissue components is achieved, in particular by constant as well as reproducible force relations.

The quality of the tissue fusion is also improved in that the electrode spacing is the same over the effective electrode length, so that a substantially exactly predetermined/better pre-definable HF current can flow between the electrodes at each longitudinal position of the electrode.

An optional, additional or independent aspect of the invention for meeting the above-mentioned object makes provision to support the separate electrode mount—preferably with a pincers- or scissor-like TFT instrument comprising ledge-shaped (i.e. axially extending, straight) electrodes—at its distal end portion or end on the respective electrode leg in a rotatable, pivotable or tilting manner, so that the electrode mount may rotate relative to an electrode leg also contrary to the pivoting movement of the latter. This means that the electrode legs are swiveled relative to each other at their proximal end portions during operating the HF instrument. On the other hand, the separate electrode mount is preferably articulated on the respective leg at its distal end portion and hence can also be rotated contrary to the closing or pivoting movement of the leg. Preferably, an (adjustable) supporting mechanism is provided in this special embodiment on the proximal end portion of the separate electrode mount between the electrode mount and the leg, so that the effective (acute) angle between the electrode mount and the leg can be adjusted.

At this point, it has to be noted that the pivot point, center of rotation or tilt point of the electrode mount on the leg not necessarily has to be arranged in the distal end portion of the electrode mount, but may also be situated in its center portion or proximal end portion.

According to a preferred further development of the invention, a number of spring elements, for example spiral springs, leaf springs or elastomer elements, are inserted between the electrode mount and the electrode/electrode array installed thereon; said spring elements keep the electrode/electrode array spaced from the electrode mount toward the opposing electrode/electrode array. The spring elements may be grouped in pairs here to simulate a larger common contact surface, wherein the spring element pairs are uniformly spaced from each other in the longitudinal direction of the electrode.

It is further preferred that the spring elements, in particular in spiral spring design, are inserted in accommodation pockets formed in the electrode mount.

At least said electrode which is installed on the separate electrode mount has a U-shape as seen in top view, and the electrode shanks—extending parallel to each other in the longitudinal direction of the legs—define a gap in the width direction of the electrode mount, in which a further lamella- or blade-shaped electrode is supported/guided in insulated manner and serves as a cutting electrode. Thus, the electrode leg as well as the separate electrode mount installed thereon also comprise a longitudinal slit which is substantially congruent with the electrode gap, through which the further cutting electrode is inserted in insulating fashion, so that the latter can be moved independently of the electrode leg/electrode mount for a cutting contact on the clamped tissue.

Finally, according to an additional or alternative aspect of the invention, a distance adjustment device may be provided on at least one of the legs, preferably on the leg which comprises the separate electrode mount, by means of which an electrode spacing existing in the closed state of the jaw part of the HF instrument can be adjusted/altered. Said distance adjustment device preferably relates to a set screw which is screwed outside the effective length of the electrodes in said one leg preferably on its distal end and is supported by the opposing leg. As an alternative to this, it is also possible to provide an adjustable stop on the hinge pivotally coupling the legs, by means of which stop the maximum pivoting angle can be adjusted in the closing direction of the legs.

At this point, reference shall be made to the fact that the spring elements may consist of a thermally conductive material and in this way preferably serve as heat transfer elements. This allows to remove heat from the electrodes through the spring elements into the electrode mount. The amount of heat which can be removed may be further set via the number of the installed spring elements.

BRIEF DESCRIPTION OF THE DRAWING FIGURES

Figure 2:
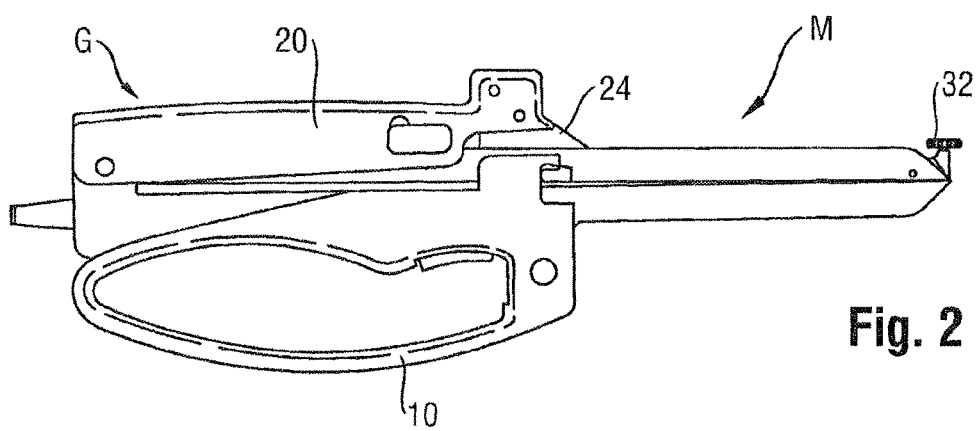
Figure 3:
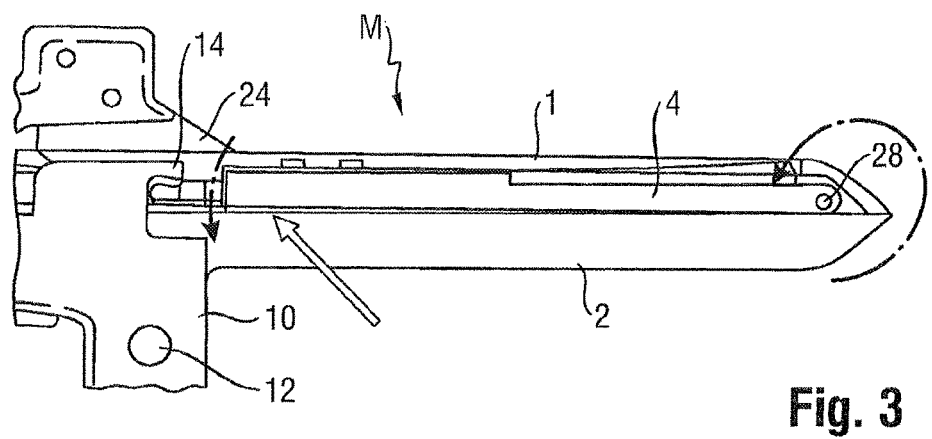
Figure 4:
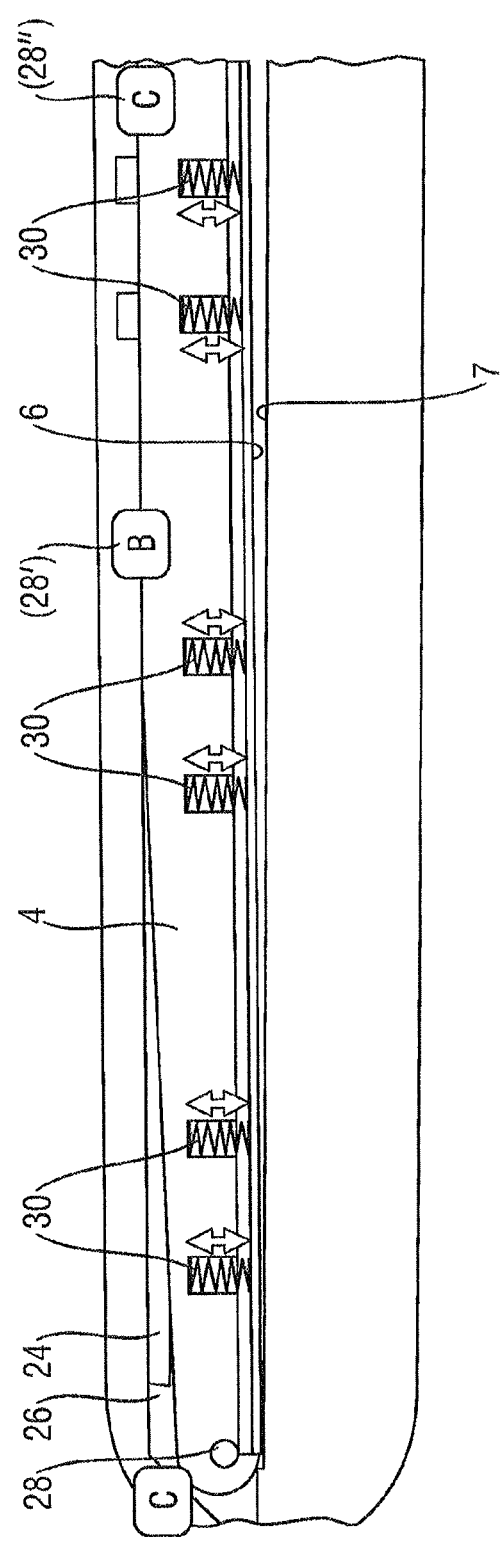
Figure 5:
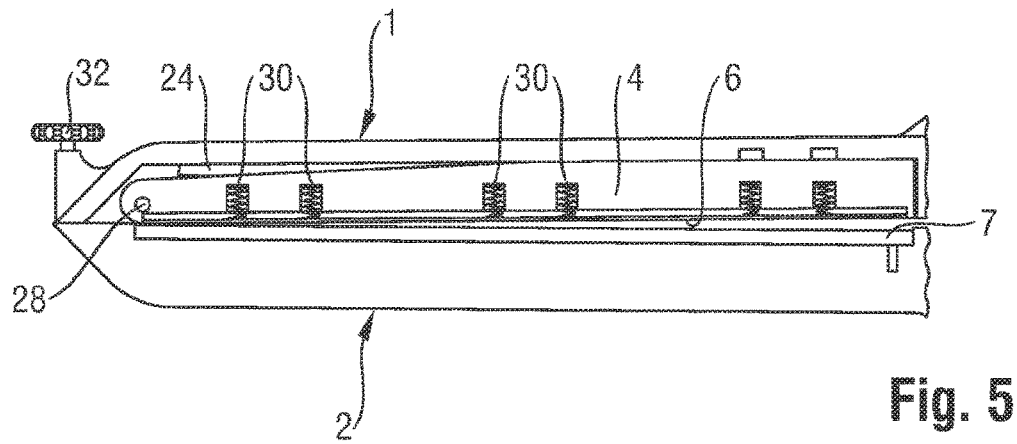
Figure 6:
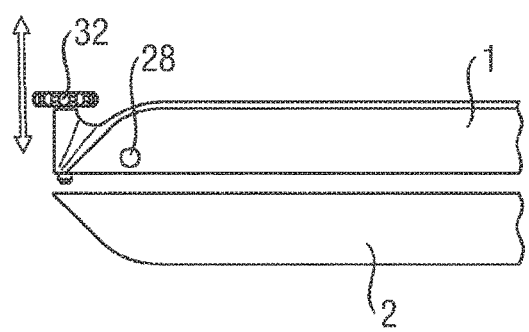
Figure 7:
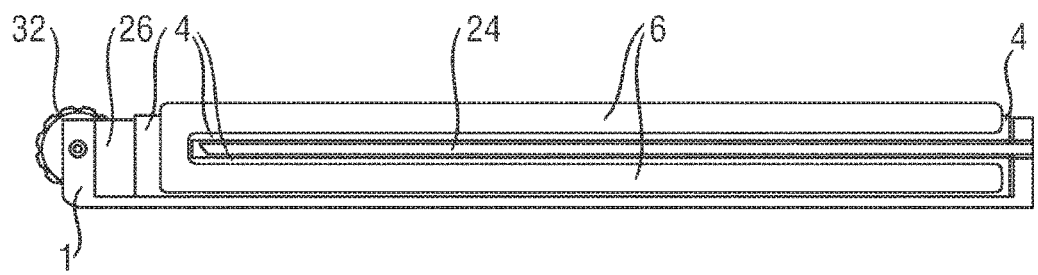

The invention will be explained in more detail below on the basis of preferred exemplary embodiments with reference to the attached drawings in which:

FIG. 1 shows a first preferred exemplary embodiment of an HF instrument according to the invention in partially broken side view without an electrode distance adjustment device, FIG. 2 shows a second preferred exemplary embodiment of an HF instrument according to the invention in a side view and comprising an electrode distance adjustment device, FIG. 3 shows a jaw part of the HF instrument according to FIG. 1 in an enlarged, partially broken side view, FIG. 4 shows the distal end portion of the jaw part according to FIG. 3 in a further enlargement, FIG. 5 shows a jaw part of the HF instrument according to FIG. 2 in an enlarged, partially broken side view, FIG. 6 shows the jaw part according to FIG. 5 in a side view with a functional representation of the electrode distance adjustment device and FIG. 7 shows a leg comprising an electrode mount articulated thereon as well as electrodes in a top view.

DETAILED DESCRIPTION

The HF instrument (in bipolar construction) exemplarily shown in FIG. 1 according to a first preferred embodiment of the invention basically comprises a jaw part M consisting of two (elongated) electrode legs 1, 2 movable relative to each other in the nature of forceps, pincers or scissors and an instrument handle G for operating (and electrically activating) the jaw part M. At least one electrode leg 1 has a separate electrode mount 4 articulated thereon (the electrode mount is pivotable relative to it), a first electrode 6 (see FIG. 4) being in turn springily/pliantly installed on said electrode mount.

Specifically, the HF instrument according to FIG. 1 consists of a first electrode leg 1 (according to FIG. 1 the upper one) and a second electrode leg 2 (according to FIG. 1 the lower one), which are articulated to each other in the manner of a hinge at their proximal ends (also corresponding to the proximal end of the HF instrument as a whole) by means of a hinge pin 8. In the distal portion of the HF instrument, the two legs 1, 2 form the jaw part M; in the proximal portion of the HF instrument, the legs 1, 2 form the instrument handle G.

A first bracket-like handle (manual lever) 10 is articulated to the second (lower) leg 2 in its center portion in the area of the instrument handle G via a pin 12; said handle is shaped with a hook- or bolt-shaped latch 14 which is able to get into a locking engagement with undercuts or studs/protrusions 16 in the center area of the first (upper) leg 1 in order to lock it in the closed position with the second leg 2. An operation button 18 is movably integrated in the bracket-like handle 10 and allows to preferably individually activate an electrical switch (not shown in further detail) for feeding HF current (for welding/sealing) to electrodes/electrode arrays on the legs 1, 2. Lastly, in the area of the instrument handle G, a second handle (manual lever) 20 is articulated to the first (upper) leg 1 or on the proximal hinge pin 8 and is operable/pivotable relative to the two legs 1, 2. In the second handle 20, a locking element or locking bolt 22 is integrated so as to be movable relative to the second handle 20, in order to be capable of being switched from an arresting position in which the locking bolt 22 interlocks the second handle 20 with the first (upper) leg 1 to a releasing position in which the second handle 20 is movable/pivotable relative to the legs 1, 2. A blade-shaped cutting electrode 24 is coupled (fixed) to the second handle 20 and can be moved by the second handle 20 relative to the legs 1, 2. It is preferred that the second handle 20 is also equipped with an operation button (likewise not shown in further detail) which can be used to (individually) activate a further electrical switch (not illustrated) for supplying the cutting electrode 24 with HF current.

FIGS. 3 and 4 show the constructional design of the jaw part M according to FIG. 1 in detail.

Accordingly, the separate electrode mount 4 is articulated on the first (upper) leg 1 preferably in the form of a retaining ledge via a hinge 28 which is arranged on the distal end portion of the first leg 1. To this end, the first leg 1 is realized with an elongated groove 26 in which the retaining ledge 4 is received so as to be able to pivot around the hinge 28. In addition, an adjusting mechanism (not shown in more detail)

is provided on the first leg 1, by means of which the relative position (or the relative angle) of the electrode mount/retaining ledge 4 with respect to the first leg 1 can be adjusted.

According to FIG. 4, tongue-shaped electrodes or electrode arrays 6, 7 are arranged in the area of the jaw part M on both legs 1, 2 so as to be opposite and parallel to each other. Specifically, the first (upper) electrode 6 is installed in electrically insulating manner on the electrode mount 4 which is preferably made from an electrically non-conductive material, whereas the second (lower) electrode 7 is installed in the present case immediately on the second leg 2 in an electrically insulating manner. Thus, the first electrode 6 along with the electrode mount 4 can pivot relative to the first leg 1 in order to be able to be aligned with respect to the second electrode 7, as will be described in more detail below.

The support of the first electrode 6 on the associated separate electrode mount 4 is realized in the present example in spring-elastic manner by means of a number of spring elements 30 which in the present case are spaced in the longitudinal direction of the electrode as pairs (or also individually). Each spring element 30 is received or supported in an accommodation pocket/blind hole, said holes or pockets being formed in the electrode mount 4. The spring elements 30 exert a biasing force on the flat side of the first electrode 6 in order to elastically support the latter toward the second electrode with respect to the electrode mount 4.

At this point, it is to be noted that an exclusively flexible support (for instance by filling the space between the electrode mount and the electrode with an insulation material) would also be possible in lieu of the springy/elastic support, where the return force preferably results from the intrinsic elasticity of the electrode. In the exemplary embodiment which is shown, the spring elements 30 are further illustrated as spiral springs. However, leaf springs or elastomer materials may also be used. Basically, it would also be conceivable to insert a resilient, preferably springy separation layer (e.g. an elastic mat) between the first electrode 6 and the electrode mount 4.

FIG. 7 shows the basic plan view of the electrodes on the first (upper) leg 1, as it is true for all presented exemplary embodiments of the invention.

According to this, the electrode/electrode array 6 which is flexibly supported on the electrode mount 4 is formed in a U-shape as seen in top view, whose shanks extend in the longitudinal direction of the legs while forming a (central) longitudinal gap. The first leg 1 is also realized with a continuous longitudinal slit which is substantially congruent to the longitudinal gap of the first electrode 6, in which the cutting electrode 24 is inserted in insulated manner and so as to be relatively movable therein.

The functioning of the HF instrument according to the first preferred exemplary embodiment of the present invention can be outlined as follows:

First, the electrode mount 4 is adjusted (swiveled on the hinge 28) by the adjusting mechanism (not further shown) with respect to the first (upper) leg 1 in such a manner that the first electrode 6 forms a defined gap width with respect to the second electrode 7 in the closed state of the HF instrument; said gap width is preferably substantially constant over the entire effective electrode length.

For the purpose of fixing a tissue to be treated in the jaw part M, the tissue parts are inserted between the electrodes 6, 7 along the legs 1, 2; then, the first handle 10 is operated to clamp/latch the first and second legs 1, 2 via the latch 14. In this position according to FIG. 1, the latch 14 reaches behind the protrusion 16 on the first (upper) leg 1 and biases the latter in its center portion against the second (lower) leg 2. As the two legs 1, 2 are hinged to each other at the proximal end via the pin 8 and have a predefined contact point (not illustrated) at their distal end, a predefined gap occurs between the legs 1, 2 whose gap width is already set at the electrode mount 4. In this latched position, the tissue to be welded/sealed is clamped between the legs 1, 2, and the two electrodes/electrode arrays 6, 7 exert a defined clamping force (clamping pressure) on the tissue.

When the push-button 18 is operated, the two mentioned electrodes 6, 7 are supplied with HF current which flows through the clamped tissue depending on the initially indicated boundary conditions and damages it in a predefined manner. By this means, a welding/sealing of the tissue will be achieved, for instance.

After having released the push-button 18, the locking bolt 22 is unlocked and hence the second handle 20 is released which is now able to swivel relative to the first leg 1 toward the second leg 2; in this process, the lamella- or tongue-shaped cutting electrode 24 fixed thereon enters the longitudinal gap between the shanks of the first electrode 6 and applies pressure on the clamped tissue. If said cutting electrode 24 is supplied with HF current now, the tissue situated between the legs 1, 2 is severed.

In this way, the clamped tissue can be welded/sealed and/or cut, for instance in order to sever projecting tissue flaps/edges.

By means of FIGS. 2, 5, 6 and 7, a second preferred embodiment of the invention will be described below. In essence only the constructional and functional differences to the first embodiment will be discussed. All further technical features correspond to the first preferred exemplary embodiment described above.

Accordingly, a leg distance adjustment device 32 (in the present case in the form of a set screw) is provided on the distal end of one leg, preferably of the first (upper) leg 1, so as to be located outside the first electrode 6/electrode mount 4. Said set screw is directly screwed into the first leg 1 and projects toward the second leg 2. Thus, the set screw 32 replaces/defines the above-described distal contact point between the two legs 1, 2. In this case, however, the contact point is not designed to be fixed, but is of flexible/adjustable nature, so that the leg distance in the area of the jaw part M can be adjusted on the closed instrument and hence can be tuned/adapted to the tissue to be treated.

The mode of operation of the HF instrument according to the second exemplary embodiment is almost the same as of the first exemplary embodiment, so that reference can be made here to the preceding text passages. An additional function, however, is represented by the leg distance adjustment device 32 which is actuated in a first step in order to adjust a specific leg distance which is matched with the tissue to be treated. Corresponding to this pre-adjustment, the adjustment device for pivoting the electrode mount 4 is operated to achieve the parallelism of the electrodes 6, 7 in the closed state of the HF instrument.

As a last point, it is referred to the fact that some technical features according to the preceding description may also be modified as described in the following.

In both exemplary embodiments, the hinge 28 between the electrode mount 4 and the first leg 1 is illustrated on a distal end position of the electrode mount. Alternatively, the hinge 28' may also be arranged in a center portion, or the hinge 28" is situated in a proximal end portion of the electrode mount 4 near the instrument handle G.

The HF instrument is shown as a manual instrument in which the legs 1, 2 also form the instrument handle G. Basically, however, it is also possible to use the fundamental principle of the invention according to the above-described introductory part of the description for a minimally invasive instrument in which the jaw part M is coupled to the instrument handle G through an interposed instrument shaft.

Finally, it is also possible to equip both legs 1, 2 with separate electrode carriers and to adjust these in a corresponding manner.

In summary and according to the invention, a preferably manually operable HF instrument in bipolar construction is provided, comprising a jaw part consisting of two electrode legs which can be moved toward each other like forceps or pincers or scissors, and an instrument handle for the mechanical operation and electrical activation of the jaw part and the jaw part electrodes, respectively. At least one electrode leg of the jaw part is provided with a separate electrode mount which is articulated thereon so as to be able to pivot relative to it, an electrode or an electrode array consisting of several serially arranged individual electrodes in turn being elastically/pliantly installed on said electrode mount.

The invention claimed is:

1. A medical HF instrument in bipolar construction comprising:
    two electrode carriers which can be moved toward each other, each electrode carrier provided with at least one longitudinally extending sealing-/welding electrode or electrode array, each longitudinally extending sealing-/welding electrode or electrode array comprising shanks that extend in a longitudinal direction of the electrode carriers, the shanks forming a longitudinal gap,
    at least one of the at least one longitudinally extending sealing-/welding electrode or electrode array being supported on a separate electrode mount by an elastic support between the electrode or electrode array and the electrode mount, and
    the electrode mount being supported on one of the electrode carriers by an articulating support between the electrode mount and the electrode carrier so that the electrode mount is rotatable, pivotable or tiltingly supported relative to said one of the electrode carriers.

2. The medical HF instrument according to claim 1, wherein the at least one longitudinally extending sealing-/welding electrode or electrode array is supported on the separate electrode mount in spring-elastic manner.

3. The medical HF instrument according to claim 1, wherein the electrode carriers are formed as electrode legs which extend in a longitudinal direction of the instrument and are coupled to or shaped with an instrument handle.

4. The medical HF instrument according to claim 3, wherein the at least one of the at least one longitudinally extending sealing-/welding electrode or electrode array is a straight electrode or electrode array extending in a longitudinal direction of the instrument.

5. The medical HF instrument according to claim 4, wherein the separate electrode mount is pivotally articulated on the distal end portion of the respective electrode leg.

6. The medical HF instrument according to claim 5, wherein at the proximal end portion of the separate electrode mount, an adjustable supporting mechanism is arranged between the separate electrode mount and the respective electrode leg, so that the effective pivoting angle between the separate electrode mount and the electrode leg can be adjusted.

7. The medical HF instrument according to claim 3, wherein the electrode/electrode array installed on the separate electrode mount has a U-shape when seen in top view, a gap in the width direction of the separate electrode mount being created between the electrode legs extending parallel to each other.

8. The medical HF instrument according to claim 7, the electrode carrier as well as the separate electrode mount installed thereon each comprise a longitudinal slit which is substantially congruent with the electrode gap, a blade-shaped cutting electrode being inserted in said slit in insulating manner, so that said cutting electrode can be moved independently of the electrode carrier and the separate electrode mount installed thereon, for a cutting engagement with any tissue clamped between the electrode carriers.

9. The medical HF instrument according to claim 1 comprising one or more spring elements inserted between the separate electrode mount and the electrode/electrode array installed thereon, said one or more spring elements keeping the electrode/electrode array spaced from the separate electrode mount toward the opposing electrode/electrode array.

10. The medical HF instrument according to claim 9, wherein said one or more spring elements are grouped in pairs in each case, the pairs being uniformly spaced from each other in the longitudinal direction of the electrodes.

11. The medical HF instrument according to claim 1 comprising a manually operable distance adjustment device provided on at least one of the electrode carriers by means of which a minimum electrode spacing can be adjusted and/or altered.

12. A medical HF instrument in bipolar construction comprising:
    two electrode carriers which can be moved toward each other, each electrode carrier provided with at least one longitudinally extending sealing-/welding electrode or electrode array,
    at least one of the at least one longitudinally extending sealing-/welding electrode or electrode array being installed on a separate electrode mount that is supported on one of the electrode carriers in a rotatable, pivotable or tilting fashion, in such a manner that said at least one longitudinally extending sealing-/welding electrode or electrode array is pliably supported on the separate electrode mount, and
    one or more spring elements inserted between the separate electrode mount and the electrode/electrode array installed thereon, said one or more spring elements keeping the electrode/electrode array spaced from the separate electrode mount toward the opposing electrode/electrode array,
    wherein the one or more spring elements are inserted in accommodation pockets formed in the separate electrode mount.

13. A medical HF instrument in bipolar construction comprising:
    two electrode carriers which can be moved toward each other, each electrode carrier provided with at least one longitudinally extending sealing-/welding electrode or electrode array,
    at least one of the at least one longitudinally extending sealing-/welding electrode or electrode array being installed on a separate electrode mount that is supported on one of the electrode carriers in a rotatable, pivotable or tilting fashion, in such a manner that said at least one longitudinally extending sealing-/welding electrode or electrode array is pliably supported on the separate electrode mount, and one or more spring elements inserted between the separate electrode mount and the electrode/electrode array installed thereon, said one or more spring elements keeping the electrode/electrode array spaced from the separate electrode mount toward the opposing electrode/electrode array, wherein the one or more spring elements are simultaneously formed to be heat conducting elements which are thermally coupled to the electrode or electrode array supported thereby, and to the separate electrode mount.

\* \* \* \* \*